(12) United States Patent
Springer, Jr.

(10) Patent No.: US 6,181,974 B1
(45) Date of Patent: Jan. 30, 2001

(54) FACIAL CONTACT ELECTRODE

(76) Inventor: George E. Springer, Jr., 1827 Oak Lake Dr., Clearwater, FL (US) 33764

( * ) Notice: Under 35 U.S.C. 154(b), the term of this patent shall be extended for 0 days.

(21) Appl. No.: 09/280,756

(22) Filed: Mar. 29, 1999

(51) Int. Cl.$^7$ .................................................. A61N 1/04
(52) U.S. Cl. ............................................................ 607/140
(58) Field of Search .................................. 607/139–141, 607/115, 149, 109, 110, 75, 48

(56) References Cited

U.S. PATENT DOCUMENTS

| | | | |
|---|---|---|---|
| 3,279,468 | * 10/1966 | Le Vine | 607/140 |
| 4,709,702 | * 12/1987 | Sherwin | 607/140 |
| 5,527,357 | * 6/1996 | Springer, Jr. | 607/140 |

* cited by examiner

*Primary Examiner*—Jeffrey R. Jastrzab
(74) *Attorney, Agent, or Firm*—Ronald E. Smith; Smith & Hopen, P.A.

(57) ABSTRACT

A facial contact electrode assembly for use in electrotherapy. A galvanic current is applied to acupuncture points of a human face by adjustable electrodes. A screw head on the distal end of the electrode comes into contact with the face of a user. The screw head is rotateably adjustable whereby rotation of the screw in a first direction causes advancement of the screw head towards the user's face and counterrotation causes retraction of the screw head. Therefore, when employing an array of electrodes for electrotherapy of the face, each individual electrode can be lengthened or shortened to adjust to the individual characteristics of the user's face. Further adjustment is automatically achieved by each electrode using a resilient conductive spring enclosed within the housing of each electrode. The spring biases the electrode against the face of the user while carrying the galvanic current from an electrical power source to the screw head.

3 Claims, 1 Drawing Sheet

FACIAL CONTACT ELECTRODE

BACKGROUND OF THE INVENTION

1. Field of the Invention

This invention relates, generally, to an improved electrode design. More particularly, it relates to an adjustable electrode for facial electrotherapy.

2. Description of the Prior Art

The aging process includes loss of tone of facial tissue; such loss of tone manifests itself in wrinkles, sagging skin, and the like. Chinese acupuncture has some utility as an effective treatment for the condition, but many people either fear acupuncture, cannot afford it, or live in areas of the country where it is not available. Moreover, if the acupuncturist does not treat the user in a comprehensive, systematic fashion, the treatment may be unsatisfactory.

The use of non-penetrating electrodes to establish galvanic currents in the facial muscle is well known in efforts to treat the loss of tone in facial tissue due to the aging process. U.S. Pat. No. 4,957,480 to Morenings describes an apparatus that electrically stimulates a muscle whereby the muscle contracts in the hope that stronger muscles beneath the skin will reduce sagging of the skin. A pair of hand-held electrodes are positioned on opposite sides of the muscle to be contracted so that current flow between the electrodes also flows through the muscle.

U.S. Pat. No. 3,279,468 to Le Vine includes a mask having a plurality of paired electrodes disposed throughout. The electrodes of each pair are closely spaced to one another and one member of the pair serves as ground so that current flows only between the paired electrodes.

The present inventor's earlier contribution to the art is described in U.S. Pat. No. 5,527,357 (1996) which discloses a means and method for applying a galvanic current to acupuncture points on a human face by electrodes mounted in a predetermined array on a mask-like assembly that overlies the face. A low voltage is applied to each electrode and facial tissue is stimulated by a galvanic current that flows between the electrode and a remote ground. A rubber plug overlies the leading end of each electrode and has an enlarged, disc-shaped leading end to ensure treatment of all areas of the face that require stimulation.

Certain limitations became apparent to the present inventor using the above-described conductive rubber plugs. To effectively provide the optimum therapy, a precise galvanic current must be applied. However, in the manufacture of the rubber plugs, variability in the raw materials led to uncertain conductive properties. It was expensive and complicated to provide the critical specifications for the injection molding process to produce a plug with the correct conducting parameters.

In the assembly and use of the earlier apparatus, the rubber plugs could be slightly pulled out of their respective cylinders to extend them to a better fit. However, the plugs would not satisfactorily hold their respective positions; they would sometimes slide away from the skin and fail to make good contact therewith. The plugs could even fall out of their respective cylinders and be lost. Moreover, natural facial oils secreted by the user diminished the conductivity of the facial plugs, thus requiring their replacement.

The contact points were biased against the face using resilient foam. However, inconsistencies in the thickness of foam from manufacturers made it difficult to consistently place the electrodes properly. In addition, with repeated use, the resiliency of the foam would diminish as the foam would compress and breakdown.

Consequently, there is a need in the art for a facial electrode apparatus that delivers a consistent level of conductivity to the face of the patient and which may be inexpensively manufactured to the necessary specifications.

There is a further need in the art for a facial electrode apparatus that securely stays within the overall assembly and does not fall out after substantial use.

There is a further need in the art for a means to evenly press the electrodes against the face of the patient and that will retain a consistent resiliency over extended use.

Another need exists for a facial electrode having a conductivity that is not diminished over time by the accumulation of facial oils from the skin of the user.

Yet another need exists for a facial electrode that holds its position after a custom adjustment has been made and that will hold its position if pressure is applied thereto.

However, in view of the prior art in at the time the present invention was made, it was not obvious to those of ordinary skill in the pertinent art how the identified needs could be fulfilled.

SUMMARY OF THE INVENTION

The present invention solves significant problems in the art by providing a facial contact electrode providing high conductivity, positional stability, durability and comfort to the patient. Furthermore, the present invention employs a design that significantly reduces the overall cost of operation including the manufacture and replacement of electrode parts.

Generally described, the present invention provides an electrode assembly for use with facial electrotherapy which includes a conductive rod rigidly mounted to a circuit board. The circuit board provides a galvanic current to the conductive rod. A resilient spring surrounds the conductive rod and is in contact with the same. A cylindrical housing slides over the spring and rod so that the housing is biased away from the circuit board by the spring. On the opposite end of the housing from which the spring is received, an internally threaded bore receives a conductive screw having an enlarged screw head adapted for contact with the face of the user. When the screw is rotated in a first direction, the screw head moves towards the face of the user. Upon counterrotation, the screw head retracts from the user's face. This adjustment allows the electrode assembly to adapt to the facial variations that exist from person to person. Furthermore, the resilient spring biases the electrode assembly against the user's face to ensure that the screw head maintains direct contact with the user's face. The screw also will not displace away from the patient's face by the application of pressure thereto.

In a preferred embodiment the circuit board is sandwiched between two non-conductive liners which form a mask which overlies the face of the user. Within the inner liner, throughbores are provided through which the cylindrical housing extends.

Because the cylindrical housing is pushed by the spring towards the face of the user, a retention means is necessary so that the cylindrical housing does not fall out of the inner liner. This may be achieved by providing an annular shoulder on the end of the cylindrical housing most proximate to the circuit board. The cylindrical housing is received through the throughbore in the inner liner whereby the diameter of the annular shoulder exceeds the diameter of the throughbore and the shoulder therefore abuts the peripheral edge of the throughbore. However, the cylindrical housing may slide back and forth within the throughbore to provide a limited range of motion for the electrode assembly.

The galvanic current flows from the circuit board to the conductive rod. The spring then conducts the galvanic current from the rod to the cylindrical housing. The cylindrical housing then conducts the current to the screw and screw head which in turn conducts the current to the face of the user for therapeutic benefits. Alternatively, should the cylindrical housing be non-conductive, the spring may conduct the galvanic current directly to the end of the screw engaged in the cylindrical housing and thus to the screw head. In any permutation, conductive materials abut each other from the circuit board to the tip of the screw head in order for the apparatus to function correctly. In a preferred embodiment, the screw head is gold plated to ensure a high level of conductivity and resistance to corrosion and oxidation, even if facial oils accumulate thereon.

In other words, the inventive structure provides a mask adapted to be worn in overlying relation to a face of a human being. The mask has a facial contact electrode assembly that includes an electrically conductive electrical circuit board that is sandwiched between a nonconductive outer liner of the mask and a nonconductive inner liner of the mask. A conductive rod is disposed in electrical communication with the electrical circuit board at a substantially perpendicular angle thereto. A conductive coil spring has a hollow core that receives the conductive rod and has a proximal end in electrical communication with the electrical circuit board. A cylindrical housing has an open proximal end that slideably receives the conductive coil spring and the conductive rod. The coil spring biases the cylindrical housing away from the electrical circuit board so that the cylindrical housing is in spaced apart relation to the electrical circuit board when the coil spring is in repose.

The cylindrical housing has internal screw threads formed therein adjacent a distal end thereof. An externally threaded screw has a screw head adapted for contact with a user's face and is in screw threaded engagement with those internal screw threads.

Galvanic current flowing through the electrical circuit board is conducted to the screw head through the conductive rod, the spring, and the screw.

The coil spring biases the cylindrical housing away from the electrical circuit board so that a first range of adjustment for differing facial shapes is provided by the coil spring, and the screw threaded engagement between the screw and the cylindrical housing provides a second range of adjustment.

The novel assembly further includes an annular shoulder formed in the proximal end of the cylindrical housing. A throughbore is formed in the inner liner, so that the cylindrical housing extends through the throughbore. The annular shoulder has a diameter greater than a diameter of the throughbore, thereby preventing the proximal end of the cylindrical housing from traveling through the throughbore under the bias provided by the coil spring.

An advantage of the invention is that the tip of the electrode that comes into contact with the user's face is not only adjustable in length, but also provides a controlled range of motion by virtue of the resilient spring. This allows configuration of the apparatus in a manner that ensures the electrode will maintain contact with the face of the user, yet prevent the electrode from being uncomfortably rigid against the user's face.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
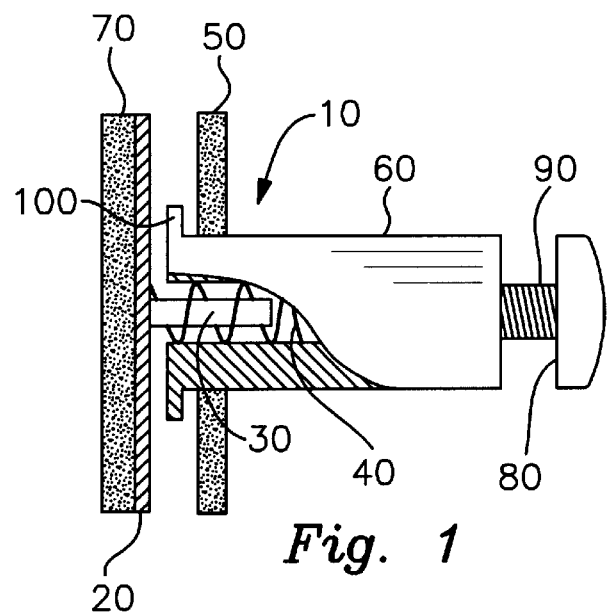
FIG. 1 is a sectional side elevational view of a preferred embodiment of the novel electrode assembly.

Referring initially to FIG. 1, it will there be seen that an illustrative embodiment of the present invention is denoted by the reference number 10 as a whole. A conductive rod 30 is rigidly fixed to a circuit board 20 at a substantially perpendicular angle. A resilient conductive spring 40 slideably receives the conductive rod 30. The spring 40 is received within a conductive cylindrical housing 60. Circuit board 20 is sandwiched between a nonconductive outer liner 70 and a nonconductive inner liner 50. The inner and outer liners are preferably constructed of a material that is inexpensive, non-corrosive, and easily cleaned such as plastic.

Figure 2:
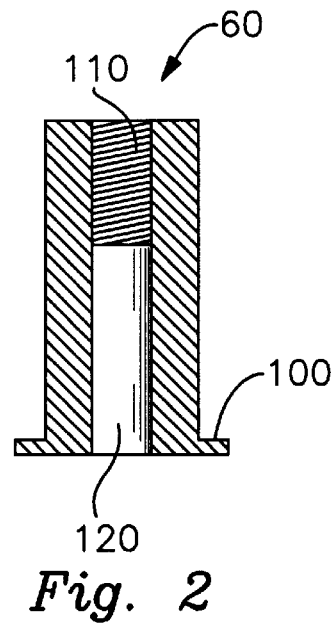
FIG. 2 is a sectional side elevation view of a preferred embodiment of the novel electrode housing.

The cylindrical housing 60 is shown in detail in FIG. 2 and comprises an upper bore 110, a lower bore 120, and an annular shoulder 100. The interior sidewalls of the upper bore 110 are internally threaded to engage a corresponding screw 90 shown in FIG. 1. The interior sidewalls of lower bore 120 are smooth and dimensioned to receive spring 40. The spring 40 is disposed against the end of screw 90 when the screw is threadably engaged in upper bore 110 of cylindrical housing 60. Annular shoulder 100 extends axially outward at the end of cylindrical housing 60 distal from upper bore 110.

Figure 3:
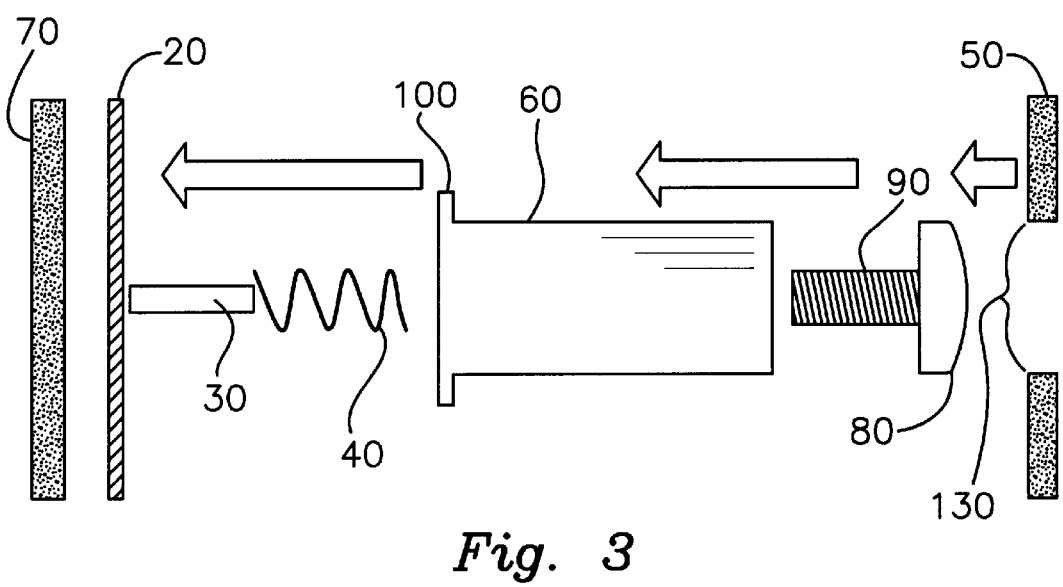
FIG. 3 is an exploded sectional side elevation view of a preferred embodiment of the novel electrode assembly.

The assembly of the apparatus is illustrated in FIG. 3 whereby the circuit board 20 is set against outer liner 70. Conductive rod 30 is rigidly secured to circuit board 20 so that galvanic current flowing through the circuit board is distributed to the conductive rod. Resilient spring 40 is axially coupled to conductive rod 30. Cylindrical housing 60 is slideably received within a throughbore 130 in the inner liner 50 whereby the annual shoulder 100 of the housing abuts the edges of the throughbore in the liner. Inner liner 50 in combination with cylindrical housing 60 is set against circuit board 20 whereby spring 40 is received within lower bore 120 of said cylindrical housing 60. Thus, spring 40 encloses conductive rod 30 and is biased between circuit board 20 and screw 90 whereby annular shoulder 100 retains cylindrical housing 60 from sliding completely out of throughbore 130. Alternatively, spring 40 may be secured to the circuit board and again within lower bore 120 of cylindrical housing 60 or to the end of screw 90 to prevent the separation of the electrode assembly from circuit board 20.

In the operation of the apparatus, a galvanic current is distributed through circuit board 20 which may selectively distribute independently variable voltages to a plurality of electrode assemblies 10. Outer liner 70 and inner liner 50 provide a nonconductive barrier to the flow of electricity throughout circuit board 20. At an individual electrode, the galvanic current flows from circuit board 20 to conductive rod 30 whereby it is conducted from spring 40 to screw 90. An annular screw head 80 conducts the galvanic current to the face of the patient. Head 80 is enlarged so that it covers a large surface area of the user's face when the electrode is in use, thereby ensuring that all areas of the face that require treatment will be treated. The relative large size of head 80 provides an error range so that the apparatus may be used with people having varying facial sizes and shapes.

In a preferred embodiment, the screw head is gold-plated for optimum conductivity and corrosion resistance. Screw 90 is rotateably mounted to cylindrical housing 60. Thus, rotation of screw 90 in a first direction causes advancement of screw head 80 towards the face of the user and counter-rotation causes retraction of the screw head. Furthermore, resilient spring 40 allows electrode apparatus 10 some restricted movement so that even if screw 90 extends into the facial plane, electrode apparatus 10 automatically adjusts to the error and retracts towards inner liner 50. This allows the electrode apparatus 10 to be adjusted so that facial contact is ensured yet the user does not suffer discomfort from a completely rigidly fixed electrode. Moreover, mere facial pressure against screw head 80 will not cause it to slip away from the face. Advantageously, facial oil accumulation on the electrode does not substantially diminish its conductivity.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A mask adapted to be worn in overlying relation to a face of a human being, said mask including a facial contact electrode assembly, comprising:

an electrically conductive electrical circuit board;

said electrically conductive electrical circuit board being sandwiched between a nonconductive outer liner of said mask and a nonconductive inner liner of said mask;

a conductive rod disposed in electrical communication with said electrical circuit board, said conductive rod being disposed at a substantially perpendicular angle to said electrical circuit board;

a conductive coil spring having a hollow core that receives said conductive rod, said conductive coil spring having a proximal end in electrical communication with said electrical circuit board;

a cylindrical housing having an open proximal end that slideably receives said conductive coil spring and said conductive rod, said coil spring biasing said cylindrical housing away from said electrical circuit board so that said cylindrical housing is in spaced apart relation to said electrical circuit board when said coil spring is in repose;

said cylindrical housing having internal screw threads formed therein adjacent a distal end of said cylindrical housing;

an externally threaded screw having a screw head adapted for contact with a user's face;

said externally threaded screw being in screw threaded engagement with said internal screw threads formed in said cylindrical housing adjacent said distal end thereof;

whereby galvanic current flowing through said electrical circuit board is conducted to said screw head through said conductive rod, said spring, and said screw;

whereby said coil spring biases said cylindrical housing away from said electrical circuit board so that a first range of adjustment for differing facial shapes is provided by said coil spring; and whereby said screw threaded engagement between said screw and said cylindrical housing provides a second range of adjustment.

2. The assembly of claim 1, wherein said screw head is gold-plated.

3. The assembly of claim 1, further comprising an annular shoulder formed in said proximal end of said cylindrical housing, and a throughbore formed in said inner liner, said cylindrical housing extending through said throughbore and said annular shoulder having a diameter greater than a diameter of said throughbore, thereby preventing said proximal end of said cylindrical housing from traveling through said throughbore under the bias provided by said coil spring.

* * * * *